United States Patent [19]

Chikashige

[11] 4,211,214
[45] Jul. 8, 1980

[54] END PLUG FITTING FOR AN ENDOSCOPE

[75] Inventor: Kiyoshi Chikashige, Tsurugashima, Japan

[73] Assignee: Asahi Kogaku Kogyo Kabushiki Kaisha, Tokyo, Japan

[21] Appl. No.: 810,462

[22] Filed: Jun. 27, 1977

[30] Foreign Application Priority Data

Jul. 1, 1976 [JP] Japan .................. 51-78278

[51] Int. Cl.² .............................................. A61B 1/00
[52] U.S. Cl. ..................................... 128/4; 128/276; 137/861
[58] Field of Search ................... 128/4, 5, 6, 7, 8, 276, 128/277, 278, 303 R, 303.1, 303.13, 303.14, 303.15; 137/205, 604, 861; 138/39

[56] References Cited

U.S. PATENT DOCUMENTS

| | | | |
|---|---|---|---|
| 2,012,363 | 8/1935 | Vogel | 128/303.14 |
| 3,124,153 | 3/1964 | Lovelace | 138/39 |
| 3,391,570 | 7/1968 | Becker et al. | 137/604 |
| 3,830,225 | 8/1974 | Shinnick | 128/2 B |
| 3,958,566 | 5/1976 | Furihata | 128/276 |

FOREIGN PATENT DOCUMENTS

| | | | |
|---|---|---|---|
| 1141999 | 9/1957 | France | 128/277 |
| 645297 | 10/1950 | United Kingdom | 137/205 |
| 720529 | 12/1954 | United Kingdom | 137/604 |

*Primary Examiner*—Robert W. Michell
*Assistant Examiner*—Arthur S. Rose
*Attorney, Agent, or Firm*—Sughrue, Rothwell, Mion, Zinn and Macpeak

[57] ABSTRACT

An end plug or fitting for an endoscope includes a mouthpiece member 1 having a central passage therethrough for the insertion of a medical instrument, such as a forceps, into a guide tube 5. The upper portion of the passage receives a sealing member 2 having a nozzle section 2a whose oblique end face confronts the mouth of a suction pipe 4 and whose inner diameter is smaller than that of the guide tube and approximately the same as the outer diameter of the instrument(s) to be inserted. Such a construction provides for ease of instrument insertion and withdrawal, good suction during insertion, and very low suction after withdrawal.

4 Claims, 5 Drawing Figures

END PLUG FITTING FOR AN ENDOSCOPE

BACKGROUND OF THE INVENTION

This invention relates to an end plug fitting for an endoscope in which the insertion and removal of a forceps or the like can be readily achieved and a sample can be extracted without dropping.

To insert or remove an implement such as a forceps, and to close the inserting inlet so that suction is maintained to enable the extraction of a body secretion or the like, a rubber strangulating member has been arranged in the inserting inlet, or several elastic sealing lids have been disposed therein having cuts intersecting the inlet axis, as disclosed in Japanese Utility Model Application Publications Nos. 29110/1972 and 26682/1975, respectively. These conventional devices are disadvantageous, however, in that the implement must be inserted by pushing it through the strangulated member or sealing lids, whereby its insertion or removal is difficult and awkward. In addition, when a sample is withdrawn with a forceps or the like, the sample often drops off and is lost as the forceps is withdrawn. Conventional mechanical devices using cocks or screws are also known, but these have intricate constructions and need special plugging means which are difficult to clean.

SUMMARY OF THE INVENTION

To overcome the above-described difficulties accompanying conventional devices, according to this invention a seal or plug member for the insertion inlet of an endoscope is provided with an opening through which a forceps or the like can be freely inserted, and the configuration of this opening and its intersection with a suction pipe are especially designed to greatly reduce the suction or negative pressure level after the removal of the inserted instrument.

More specifically, a suction passage forms a T intersection with a central passage through the end plug of an endoscope. The central passage is narrowed or necked down proximate the intersection to the approximate diameter of a forceps or the like to be inserted therethrough, and the necked down portion has an oblique face confronting the suction passage.

DETAILED DESCRIPTION OF THE PREFERRED EMBODIMENT

Figure 1:
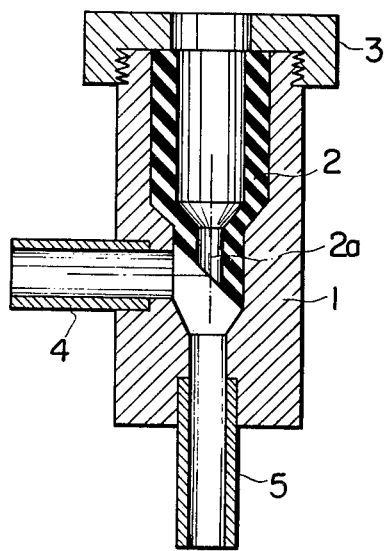
FIG. 1 shows a sectional elevation of an endoscope end plug or fitting according to this invention.

Referring now to FIG. 1, a guide tube 5 for a forceps or the like is connected to a mouth piece in axial alignment with an implement insertion inlet thereabove. A suction pipe 4 is connected to the mouth piece 1 such that its axis intersects that of the guide tube 5. Reference numeral 2 designates a sealing member inserted into the mouth piece through the implement insertion inlet such that it is in close contact with the cylindrical inner wall of the mouth piece. The sealing member is fixedly secured in the mouth piece. The sealing member is fixedly secured in the mouth piece 1 by a nut 3, and its inner end is formed into a nozzle section 2a whose inside diameter is substantially equal to the diameter of a forceps or the like to be inserted. The nozzle section has an oblique end surface obtained by cutting the necked down end of the sealing member on the diagonal, and is positioned in the mouth piece 1 such that the center of the oblique end surface opening is coincident with the central axis of the suction pipe 4.

The oblique end surface of the nozzle section 2a may be flat or curved. Further, if the inside diameter of the intermediate portion of the mouth piece 1 is larger than the outside diameter of the nozzle section 2a, and if the sealing member 2 is made of an elastic material such as rubber, an implement whose diameter is larger than the inside diameter of the nozzle section 2a may be forceably inserted therethrough owing to the expansion capability provided by the "loose fit".

Figure 2:
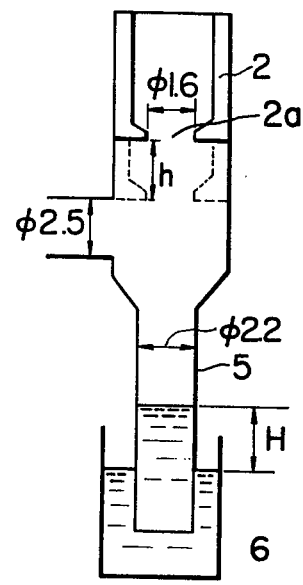
FIG. 2 shows a schematic sectional view of a first experimental model used in developing the invention.
Figure 3:
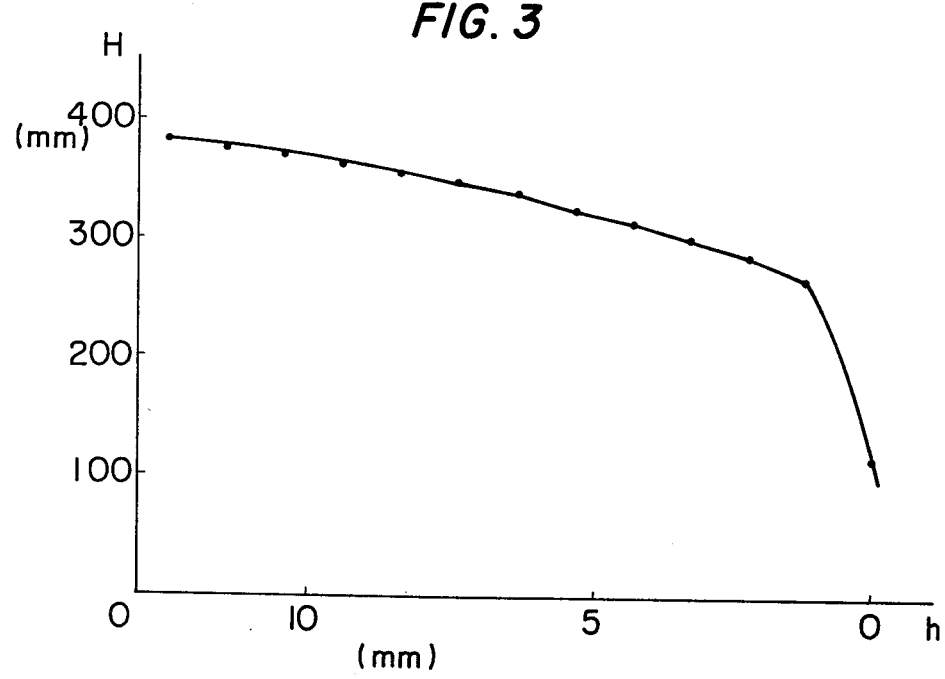
FIG. 3 shows a plot of test results obtained using the model shown in FIG. 2.

FIG. 2 shows a schematic sectional view of an experimental model involved in the development of the invention, and FIG. 3 is a graph of test results obtained with the model shown in FIG. 2. The model was designed so that the sealing member 2 could be vertically adjusted within the mouth piece member 1, whereby the distance h between the upper end of the suction pipe 4 and the bottom end of the nozzle section 2a could be varied. The end of the guide tube 5 was immersed in a water tank 6. The curve plotted in FIG. 3 shows the height H of the water column in the tube 5 with respect to variations in the height h of the sealing member 2, with a constant suction applied.

Figure 4:
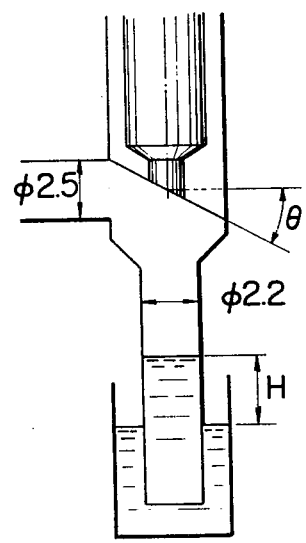
FIG. 4 shows a schematic sectional view of a second experimental model used in developing the invention.
Figure 5:
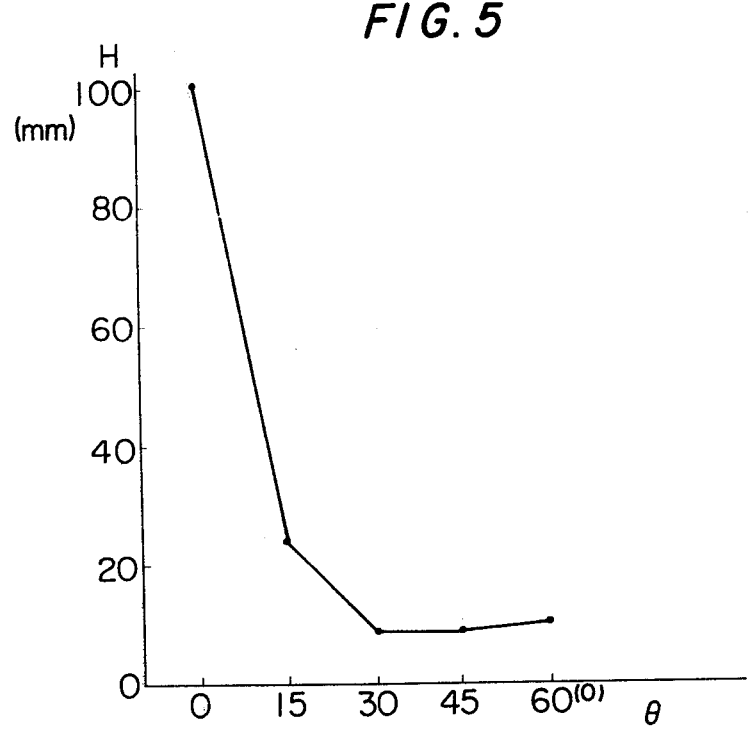
FIG. 5 shows a plot of test results obtained using the model shown in FIG. 4.

FIG. 4 shows a schematic sectional view of another experimental model involved in the development of the invention, and FIG. 5 is a graph of test results obtained with the model shown in FIG. 4. In this model the sealing member 2 is held so that the distance h is substantially zero (0), but the oblique angle $\theta$ is gradually varied. The curve plotted in FIG. 5 shows variations in the height H of the water column as a function of the oblique angle $\theta$.

Consider the case where two pipes are connected together longitudinally, and a suction pipe is connected to the intersection of the first two pipes in a T-junction manner. The ratio of the exhaust gas sucked through one of the two connected pipes to the gas sucked through the other pipe is then roughly proportional to the ratio of the flow resistances of the two connected pipes, which is a function of their respective diameters and lengths.

Where, as shown in FIG. 2, the diameter of the nozzle section 2a of the sealing member 2 is relatively small and provides a high flow resistance, the internal (vacuum) pressure in tube 5 increases substantially in proportion to the ratio of the area of the nozzle section opening 2a to the area of the guide tube opening 5. However, as the distance h is decreased the vacuum or suction pressure in the tube 5 is also reduced, and drops off sharply as h approaches zero, as shown in FIG. 3. As can easily be seen from FIG. 3, however, even if the distance h becomes zero the vacuum pressure in tube 5 still remains above 100 mm.

The test results obtained with the experimental model shown in FIG. 2 led to the further development shown in FIG. 4, wherein the distance h is zero and the end of the nozzle section 2a is cut obliquely such that the nozzle outlet is positioned in the vicinity of the center of the suction pipe 4. In this case, the gas or fluid drawn through and exiting from the nozzle section 2a is aimed or directed toward the suction pipe so that the fluid flow conditions are maintained more stable. The relatively high velocity fluid jet at the nozzle opening sweeps past the mouth of and is applied to the guide tube 5, and causes the suction pressure therein to approach zero when the oblique angle θ lies in a range of from 30 degrees to 60 degrees.

As is thus apparent, with an end plug device as shown in FIG. 1, when a forceps or the like is inserted into the tube 5 through the nozzle section 2a, the gap between the forceps and the nozzle section is very narrow such that the latter is almost completely closed and its flow resistance is therefore very high, while there is ample space between the forceps and the inner wall of the guide tube. The suction through the pipe 4 therefore causes the body liquid or gas to be examined to be extracted through the tube 5 as desired.

When the forceps or other instrument is withdrawn through the end plug, however, to thereby open the nozzle section 2a, the vacuum pressure in the tube 5 is greatly reduced. For suction pressures typically used in such devices, for example, 10-50 cmHg, the reduced vacuum pressures in the tube 5 can be substantially disregarded, even if suction is still applied to the pipe 4. This prevents any body gas in the body cavity of a human being from being discharged to the exterior through the tube 5 during a continuous sucking action in response to any continuing vacuum pressure, avoids the undue suction withdrawal of unneeded body fluids, and minimizes any patient discomfort. Furthermore, when a tissue or specimen sample is extracted with a brush or forceps, the sample is not "wiped" or squeezed as the tip of the instrument passes through the nozzle section, whereby the dropping or loss of the sample is minimized.

What is claimed is:

1. An end plug fitting for an endoscope adapted for the insertion and removal of a medical instrument, such as a forceps, therethrough, comprising:
   (a) a mouthpiece member having a central passage therethrough defining an instrument insertion opening at one end and an instrument guide channel at the other end,
   (b) a suction passage defined in the mouthpiece member intersecting the central passage, and
   (c) a tubular sealing member disposed in the central passage in the insertion opening end thereof and including a nozzle portion adjacent the suction passage intersection,
   (d) the nozzle portion having an inner diameter substantially equal to the diameter of a medical instrument to be inserted therethrough and smaller than the inner diameter of the guide channel, and an end face formed such that the angle between said end face and the axis of the central passage is oblique, said end face defining an oval central passage opening, the sealing member being rotationally oriented in the central passage such that the oval opening in the oblique end face of the nozzle portion confronts the suction passage.

2. An end plug fitting as defined in claim 1, wherein the center of the oval nozzle opening is substantially coincident with the suction passage axis.

3. An end plug fitting as defined in claim 1, wherein the suction passage is substantially perpendicular to the central passage, and the angle of obliquity is from 30° to 60°.

4. An end plug fitting as defined in claim 2, wherein the suction passage is substantially perpendicular to the central passage, and the angle of obliquity is from 30° to 60°.

* * * * *